United States Patent [19]
Drake et al.

[11] Patent Number: 6,013,849
[45] Date of Patent: Jan. 11, 2000

[54] TOLUENE DISPROPORTIONATION PROCESS USING A ZEOLITE/TUNGSTEN CARBIDE CATALYST

[75] Inventors: Charles A. Drake, Nowata; An-hsiang Wu, Bartlesville, both of Okla.

[73] Assignee: Phillips Petroleum Company, Bartlesville, Okla.

[21] Appl. No.: 09/220,959

[22] Filed: Dec. 28, 1998

[51] Int. Cl.$^7$ ........................................... C07C 5/22
[52] U.S. Cl. ............................................. 585/475
[58] Field of Search .................... 585/475, 470

[56] References Cited

U.S. PATENT DOCUMENTS

| | | | |
|---|---|---|---|
| 4,219,445 | 8/1980 | Finch | 252/443 |
| 4,259,537 | 3/1981 | Chin | 585/467 |
| 4,325,843 | 4/1982 | Slaugh et al. | 252/443 |
| 4,532,226 | 7/1985 | Chin | 502/71 |
| 5,120,692 | 6/1992 | Beck | 502/60 |
| 5,330,944 | 7/1994 | Sherif et al. | 502/64 |
| 5,451,557 | 9/1995 | Sherif | 502/177 |
| 5,776,852 | 7/1998 | Wu et al. | 502/177 |

FOREIGN PATENT DOCUMENTS

| | | | |
|---|---|---|---|
| 1343172 | 1/1974 | United Kingdom | 260/116 |

*Primary Examiner*—Walter D. Griffin
*Assistant Examiner*—Thuan D. Dang

[57] ABSTRACT

Catalysts that are zeolite-based and contain tungsten carbide. A tungsten carbide/zeolite catalyst useful in the disproportionation of sulfur containing toluene. A method for preparing a tungsten carbide/zeolite catalyst. A method for disproportionation of sulfur-containing toluene in the presence of a tungsten carbide/zeolite catalyst. An acid-leached zeolite impregnated with tungsten carbide as a catalyst composition for use in converting hydrocarbons. A method for preparing a catalyst composition of acid-leached zeolite impregnated with tungsten carbide. A method for contacting a hydrocarbon feedstock with a catalyst composition of acid-leached zeolite impregnated with tungsten carbide under conditions for converting the hydrocarbons.

13 Claims, No Drawings

TOLUENE DISPROPORTIONATION PROCESS USING A ZEOLITE/TUNGSTEN CARBIDE CATALYST

BACKGROUND OF THE INVENTION

The invention relates to catalyst compositions that are zeolite-based and contain tungsten carbide. In one of its aspects the invention also relates to a process for increasing the conversion of a cracked gasoline feedstock to ethylene, propylene and BTX (benzene, toluene and xylenes) in the presence of an improved zeolite-based catalyst material. In another of its aspects the invention relates to a process for the disproportionation of sulfur-containing toluene to produce benzene and xylenes.

It is known to catalytically crack non-aromatic gasoline boiling range hydrocarbons, particularly hydrocarbons such as paraffins and olefins, to lower olefins (such as ethylene and propylene) and aromatic hydrocarbons (such as benzene, toluene and xylenes) in the presence of catalysts which contain a zeolite (such as ZSM-5), as is described in an article by N.Y. Chen et al. in Industrial & Engineering Chemistry Process Design and Development, Volume 25, 1986, pages 151–155. The reaction products of the catalytic cracking processes contain a multitude of hydrocarbons such as unconverted $C_5+$ alkanes, lower alkanes (methane, ethane, propane). lower alkenes (ethylene and propylene), $C_6$–$C_8$ aromatic hydrocarbons (benzene, toluene, xylenes and ethylbenzene) and $C_9+$ aromatic hydrocarbons. It can be desirable to further process the product from a catalytic gasoline cracking operation to increase the yield of compounds that, in a current market, are relatively more valuable than other products of gasoline cracking. The cracking operation yield of lower olefins (such as ethylene and propylene) and BTX (benzene, toluene, xylene and ethylbenzene) aromatics, for example, can be increased using the improved zeolite catalyst compositions of this invention.

Disproportionation of toluene using a catalyst that contains zeolite and tungsten is shown in U.S. Pat. No. 4,532,226. The catalyst disclosed also contains phosphorus and the tungsten is not in the form of tungsten carbide.

SUMMARY OF THE INVENTION

It is an object of this invention to provide catalysts based on zeolite combined with tungsten carbide that are useful to at least partially convert hydrocarbons to ethylene, propylene and BTX aromatics and in the disproportionation of toluene.

Another object of this invention is to provide an improved zeolite-based catalyst that contains tungsten carbide that can be utilized in the conversion of hydrocarbons to give an improved yield of lower olefins and BTX aromatics.

Another object of this invention is to provide an improved zeolite-based catalyst that contains tungsten carbide that can be utilized in the disproportionation of toluene in the presence of sulfur.

A further object of this invention is to provide a method for making improved zeolite-based catalyst that utilized in the conversion of hydrocarbons yields a product having an improved yield of lower olefins and BTX aromatics.

A still further object of this invention is to provide a method for making improved zeolite-based catalyst that can be utilized in the disproportionation of toluene in the presence of sulfur to provide yields of benzene and xylenes.

The inventive composition is a mixture of a zeolite and tungsten carbide. The composition is prepared by contacting a zeolite with a solution of guanidine hydrochloride and tungsten hexachloride, drying the resulting slurry and calcining the dried mixture. Contacting a silica-bound ZSM-5 zeolite with the solution of tungsten hexachloride in guanidine hydrochloride provides a composition that can be used in the disproportionation of toluene. Contacting an acid-treated ZSM-5 zeolite with the solution of tungsten hexachloride in guanidine hydrochloride provides an inventive composition that can be used in the conversion of non-aromatic hydrocarbons to lower olefins by subjecting a hydrocarbon feedstock containing non-aromatics to conversion conditions in the presence of the inventive composition.

Other objects and advantages of the invention will become apparent from the detailed description and the appended claims.

DETAILED DESCRIPTION OF THE INVENTION

The zeolite material used in making the inventive composition can be any zeolite which when contacted with non-aromatic hydrocarbons under suitable operating conditions is effective in the conversion of non-aromatic hydrocarbons to aromatic hydrocarbons or which when contacted with toluene under suitable conditions is effective in the disproportionation of the toluene. Preferably, the zeolite has a constraint index (as defined in U.S. Pat. No. 4,097,367, which is incorporated here by reference) in the range of about 0.4 to about 12, more preferably about 2 to about 9. Generally the molar ratio of $SiO_2$ to $Al_2O_3$ in the crystalline framework of the zeolite is at least about 5:1 and can range up to infinity. Preferably the molar ratio of $SiO_2$ to $Al_2O_3$ in the zeolite framework is about 8:1 to about 200:1, more preferably about 12:1 to about 100:1. Preferred zeolites include ZSM-5, ZSM-8, ZSM-11, ZSM-12, ZSM-35, ZSM-38 and mixtures thereof. Some of these zeolites are also known as "MFI" or "Pentasil" zeolites. The presently most preferred zeolite is ZSM-5.

A critical aspect of the disproportionation process of this invention is the use of a catalyst containing a silica-bound ZSM-5. The silica-bound ZSM-5 can be prepared by calcining a mixture of ZSM-5 zeolite and a silica (such as Ludox AS-40, an aqueous colloidal silica sol made by E. I. Du Pont de Nemours & Co.).

Although any suitable means or method can be used to combine the zeolite with silica it is preferred to mix approximately equal amounts of the zeolite and a silica sol, treat the mixture at an elevated temperature in the range of about 100° C. to about 150° C. for a period of time of about 1 hour to about 6 hours and then further elevate the temperature to a range of about 475° C. to about 625° C., more preferably about 525° C. to about 575° C., for a period of time of about 3 hours to about 10 hours to provide a calcined silica-bound ZSM-5 powder.

A critical aspect of the aromatization process of this invention is the use of a catalyst containing a zeolite material that has been treated with an acid. As used in this specification and in the claims, the term "acid treated zeolite", or "acid leached zeolite", is defined as a zeolite starting material that has been treated with an acid.

Any suitable means or method can be used to treat the zeolite starting material with acid. It is preferred for the zeolite to be soaked in an acid solution by any suitable means known in the art for contacting the zeolite with such acid solution. The acid solution used to treat the zeolite can be a solution of any acid that provides leaching of aluminum atoms from the zeolite particles. Preferably, the acid concentration in this solution is about 1–10 equivalents per liter. Sulfuric, phosphoric, nitric and hydrochloric acids are among the acids suitable for treating the zeolite. The preferred acid solution is aqueous hydrochloric acid. The zeolite is soaked in the acid solution (preferably at a temperature within the range of about 50–100° C.) for a period of up to about 15 hours, but, preferably, in a range of about 0.1 hour to about 12 hours. The acid treated zeolite resulting from the soaking is washed free of the acid.

After the acid treated zeolite is washed free of the acid, the resulting product is exposed, by any suitable method known in the art, to a gas atmosphere under temperature and pressure conditions and for a period of time that is suitable to provide a desired heat treated product.

The gas used in the heat treatment of the acid treated zeolite can be selected from the group consisting of inert gases (nitrogen, helium, argon and the like), reducing gases (carbon monoxide, hydrogen and the like), air, oxygen and steam. The preferred gas is selected from among air, oxygen, nitrogen, steam and mixtures thereof. Most preferably, the treatment gas is selected from among air, oxygen, nitrogen and mixtures of two thereof.

Generally, this heat treatment can be conducted at a pressure in a range from below atmospheric pressure to about 1000 pounds per square inch absolute (psia). More typically, however, the pressure range is from about atmospheric to about 100 psia. The temperature of this heat treatment is generally in the range of about 250° C. to about 800° C. Preferably, this temperature range is from about 350° C. to about 700° C. and, most preferably, the temperature of this heat treatment is in a range of about 450° C. to about 600° C.

The time period for conducting this heat treatment must be sufficient to provide a material that is substantially dry, i.e., free of water. Generally, the period of time during which the acid treated zeolite is exposed to treating gas at appropriate conditions of temperature and pressure can range from about 0.1 hour to about 30 hours. Preferably, this heat treatment is conducted for a time period in the range of about 0.25 hour to about 20 hours and, most preferably, from about 0.5 hour to about 10 hours.

After the heat treatment, either the calcined silica-bound ZSM-5 powder or the washed, acid treated zeolite is further treated to provide a tungsten-containing catalyst composition. The tungsten can be incorporated into the zeolite by any suitable means for incorporating metallic elements into a substrate material. A preferred method of incorporation is the use of any incipient wetness technique for impregnating the zeolite substrate with the metal. The preferred method uses a liquid impregnation solution containing the desired concentration of tungsten to ultimately provide a final catalyst composition having the desired concentration of tungsten.

It is particularly desirable to use an aqueous or non-aqueous solution of either (a) elemental tungsten or (b) a tungsten salt for the impregnation of the zeolite, but any suitable tungsten-containing solution can be used. The preferred impregnation solution is a non-aqueous solution formed by dissolving a tungsten salt, preferably tungsten hexachloride, in an ethanolic solution of guanadine hydrochloride. If necessary, the solution can be mildly acidic to aid in the dissolution of the metal salt.

The amount of tungsten incorporated or impregnated into the zeolite should provide a concentration effective to assure disproportionation of toluene or predetermined aromatics and olefin conversion yields with low coke production employing the catalyst composition in the conversion of a hydrocarbon feedstock. Generally, the weight percent of tungsten present in the impregnated acid treated zeolite is in a range of up to about 10 weight percent of the impregnated acid treated zeolite. The preferred concentration of tungsten in the impregnated acid treated zeolite is in the range of about 0.05 to about 8 weight percent and, more preferably, from about 0.1 to about 6 weight percent.

The catalyst composition described herein can also contain an inorganic binder (also called matrix material) preferably selected from among alumina, silica, alumina-silica, aluminum phosphate, clays (such as bentonite) and mixtures thereof. The content of the impregnated acid treated zeolite component of the mixture of impregnated acid treated zeolite and inorganic binder is about 50–99 (preferably about 50–80) weight percent. The content of the above-listed inorganic binders in the mixture of impregnated acid treated zeolite and inorganic binder is about 1–50 weight percent. Generally, the impregnated acid treated zeolite and organic binder components are compounded and subsequently shaped (such as by pelletizing, extruding or tableting). Generally the surface area of the compounded composition is about 50–700 $m^2/g$, and the particle size is about 1–10 mm.

The impregnated zeolite can be subjected to heat treating by which it is exposed by any suitable method known in the art to a gas atmosphere under temperature and pressure conditions and for a period of time to provide a desired heat treated material. The gas used in the heat treatment of the zeolite can be selected from the group consisting of inert gases (nitrogen, helium, argon and the like), reducing gases (carbon monoxide, hydrogen and the like), air, oxygen and steam. The preferred gas is selected from among air, oxygen, nitrogen, steam and mixtures thereof. Most preferably, the treatment gas is selected from among air, oxygen, nitrogen and mixtures of two thereof.

Generally, this heat treatment can be conducted at a pressure in a range from below atmospheric pressure to about 1000 pounds per square inch absolute (psia). More typically, however, the pressure range is from about atmospheric to about 100 psia. The temperature of this heat treatment is generally in the range of about 500° C. to about 1000° C. Preferably, this temperature range is from about 600° C. to about 900° C. and, most preferably, the temperature of this heat treatment is in a range of about 650° C. to about 850° C.

The time period for conducting this heat treatment must be sufficient to provide a material that is substantially dry, i.e., free of water. Generally, the period of time during which the acid treated zeolite is exposed to treating gas at appropriate conditions of temperature and pressure can range from about 0.1 hour to about 30 hours. Preferably, this heat treatment is conducted for a time period in the range of about 0.25 hour to about 20 hours and, most preferably, from about 0.5 hour to about 10 hours.

In the process of this invention that applies most specifically to the conversion of cracked hydrocarbon feedstocks to aromatic hydrocarbons the preferred feedstocks are cracked hydrocarbon feedstocks from the catalytic cracking (e.g., fluidized catalytic cracking and hydrocracking) of gas oils and the thermal cracking of light hydrocarbons, naphthas, gas oils, reformates and straight-run gasoline. The cracked gasoline feedstock generally comprises hydrocarbons containing 2–16 carbon atoms per molecule chosen from among paraffins (alkanes) and/or olefins (alkenes) and/or naphthenes (cycloalkanes). The most preferred feedstock for this process of this invention is a cracked gasoline derived from the fluidized catalytic cracking of gas oil, suitable for use as at least a gasoline blend stock generally having a boiling range of from about 80° F. to about 430° F. The boiling range of the cracked hydrocarbon feedstock is determined by the standard ASTM method for measuring the initial boiling point and the end-point temperatures. Generally the content of paraffins exceeds the combined content of olefins, naphthenes, and aromatics (if present). The process of this invention is principally directed to the aromatization of a cracked hydrocarbon feedstock. It is specifically noted that the alkylation of aromatic compounds is substantially absent because either the reaction does not take place or insubstantial quantities of aromatics are present in the feedstock in the process of this invention.

Cracked hydrocarbon feedstock and the catalyst composition can be contacted within a reaction zone in any suitable manner. The contacting can be operated as a batch process or, preferably, as a continuous process. In a continuous process a solid catalyst bed, a moving catalyst bed or a fluidized catalyst bed can be employed. Each of these modes of operation has known advantages and disadvantages so that one skilled in the art can select the mode most suitable for a particular feedstock and catalyst.

Contacting the hydrocarbon feedstock and the catalyst composition is preferably carried out in a conversion reaction zone which contains the catalyst composition employing reaction conditions that promote the formation of olefins, preferably light olefins, and aromatics, preferably BTX, from at least a portion of the hydrocarbons in the cracked hydrocarbon feedstock. The reaction temperature employed in the contacting is in the range of from about 400° C. to about 900° C., preferably, from about 500° C. to about 800° C. and, more preferably, from 600° C. to about 700° C. The pressure employed in the contacting can range from subatmospheric up to about 500 psia and, preferably, from about atmospheric to about 400 psia.

The flow rate at which the cracked hydrocarbon feedstock is charged to the conversion reaction zone for contact with the catalyst composition is selected to provide a weight hourly space velocity (WHSV) in a range having an upward limit of about 1000 hour$^{-1}$. The term "weight hourly space velocity", as used herein, shall mean the numerical ratio of the rate at which a cracked hydrocarbon feedstock is charged to the conversion reaction zone in pounds per hour divided by the pounds of catalyst contained in the conversion reaction zone to which the hydrocarbon is charged. The preferred WHSV of the feed to the conversion reaction zone, or contacting zone, can be in the range of from about 0.25 hour$^{-1}$ to about 250 hour$^{-1}$ and, more preferably, from about 0.5 hour$^{-1}$ to about 100 hour$^{-1}$.

In the process of this invention that applies most specifically to the disproportionation of toluene the feedstocks often have relatively high sulfur content retained from the gasoline streams from which the toluene was obtained. The process of disproportionation of this material requires a catalyst that is sufficiently sulfur tolerant/resistant that contact with sulfur does not result in irreversible catalytic deactivation. The toluene feedstocks useful in this invention can have sulfur content in a range up to about 500 ppm. The process of this invention is principally directed to the production of mixed xylenes and benzene, products of a higher economic value than toluene.

Toluene feedstock and the catalyst composition can be contacted within a reaction zone in any suitable manner. The contacting is preferably operated as a continuous process. In the continuous process a solid catalyst bed, a moving catalyst bed or a fluidized catalyst bed can be employed. Each of these modes of operation has known advantages and disadvantages so that one skilled in the art can select the mode most suitable for a particular feedstock and catalyst.

Contacting the toluene feedstock and the catalyst composition is preferably carried out in a conversion reaction zone which contains the catalyst composition employing reaction conditions that promote the formation of benzene and xylenes. The reaction temperature employed in the contacting is in the range of from about 350° C. to about 600° C., preferably, from about 400° C. to about 550° C. and, more preferably, from 425° C. to about 525° C. The pressure employed in the contacting can range from subatmospheric up to about 1000 psia and, preferably, from about 350 psia to about 650 psia.

The flow rate at which the toluene feedstock is charged to the reaction zone for contact with the catalyst composition is selected to provide a weight hourly space velocity (WHSV) in a range having an upward limit of about 1000 hour$^{-1}$. The term "weight hourly space velocity", as used herein, shall mean the numerical ratio of the rate at which a toluene feedstock is charged to the conversion reaction zone in pounds per hour divided by the pounds of catalyst contained in the conversion reaction zone to which the hydrocarbon is charged. The preferred WHSV of the feed to the conversion reaction zone, or contacting zone, can be in the range of from about 0.25 hour$^{-1}$ to about 250 hour$^{-1}$ and, more preferably, from about 0.5 hour$^{-1}$ to about 100 hour$^{-1}$.

The following examples are presented to further illustrate this invention and are not to be construed as unduly limiting its scope.

EXAMPLE I

This example illustrates the preparation of catalysts which were subsequently tested as catalysts in the conversion to ethylene, propylene and BTX of a gasoline sample, which had been produced in a commercial fluidized catalytic cracking unit (FCC).

Catalyst A- Zeolite

Catalyst A was a commercially available ZSM-5 catalyst provided by United Catalysts Inc. of Louisville, Ky. under their product designation "T-4480".

Catalyst B- Acid Leached Zeolite

A commercially available ZSM-5 catalyst (provided by United Catalysts Inc. of Louisville, Ky. under their product designation "T-4480" was treated by acid leaching. To provide an acid leached catalyst the catalyst was soaked in a 6N aqueous HCL solution for two hours at a constant temperature of about 90° C. After soaking, the catalyst was separated from the acid solution and thoroughly washed with water and dried. The acid soaked, washed and dried catalyst was calcined at atmospheric pressure and a temperature of about 525° C. for about four hours.

Catalyst C- Tungsten Impregnated and Heat Treated Acid Leached Zeolite

A 20 gram quantity of the above-described acid leached ZSM-5 catalyst was impregnated by an incipient wetness technique with a 13.14 gram quantity of a solution containing 8.6 grams of guanidine and 12 grams of tungsten chloride in 75 ml of ethanol solvent. This impregnated, acid leached zeolite was then dried and calcined in a helium atmosphere at atmospheric pressure and a temperature of about 750° C. for about 6 hours. The final product contained 6.994 weight percent tungsten as tungsten carbide.

EXAMPLE II

This example illustrates the use of the Zeolite materials described in Example I as catalysts in the conversion of a gasoline feed to incremental aromatics such as benzene, toluene and xylene (BTX) and lower olefins (ethylene and propylene).

For each of the test runs, a 5.0 g sample of the catalyst materials described in Example I was placed into a stainless steel tube reactor (length: about 18 inches; inner diameter: about 0.5 inch). Gasoline boiling range feedstock from a catalytic cracking unit of a refinery was passed through the reactor at a flow rate of about 14 ml/hour, at a temperature of about 600° C. and at atmospheric pressure (about 0 psig). The formed reaction product exited the reactor tube and passed through several ice-cooled traps. The liquid portion remained in these traps and was weighed. The volume of the gaseous portion which exited the traps was measured in a "wet test meter". Liquid and gaseous product samples (collected at hourly intervals) were analyzed by means of a gas chromatograph. Results of the test runs for Catalysts A through C are summarized in Table I. All test data were obtained after 8 hours on stream.

TABLE I

Conversion of a Gasoline Feed

| Catalyst | Description | BTX Yield Wt %[1] | Ethylene Yield Wt %[1] | Propylene Yield Wt %[1] |
|---|---|---|---|---|
| A (Control) | Zeolite | 41 | 6.6 | 6.4 |
| B (Control) | Acid Leached Zeolite | 48 | 5.8 | 4.0 |
| C (Invention) | Acid Leached Zeolite and Tungsten | 41 | 8.6 | 9.2 |

[1]Weight percent of product

The test data presented in Table 1 show that the process of this invention produced considerably more ethylene and propylene than either Control Catalyst A or Control Catalyst B. In current product pricing the increased yields of ethylene and propylene provide a significant increase in the value of the product produced according to the invention as compared to either of the control processes.

EXAMPLE III

This example illustrates the preparation of catalysts which were subsequently tested as catalysts in the disproportionation to benzene and xylenes of toluene that contained sulfur.

Catalyst D- Zeolite without Promoter

A quantity of 25 grams of PZ-2/50H zeolite and a quantity of 25 grams of Ludox As-40 were intermixed. The temperature of the mixture was increased to 125° C. and held for 3 hours. The temperature was then increased to 538° C. and held for 6 hours. The mixture was cooled and collected.

Catalyst E- Zeolite with Platinum Promoter

A quantity of 14 grams of a solution of chloroplatinic acid ($H_2PtCl_6$) was mixed with 27.6 grams of Catalyst D and treated at a temperature of 538° C. for 6 hours. A quantity of 27.23 grams of zeolite containing 0.098 wt % platinum was recovered.

Catalyst F- Zeolite with Tungsten Carbide Promoter

A quantity of 5.2 grams of a solution of ammoniumtungstate (($NH_4)_4H_2W_{12}O_{40}$) was mixed with 10.0 grams of Catalyst D. The temperature of the mixture was raised 3° C./min to 750° C. with a flow of 200 mL/min of helium and was then treated at a temperature of 750° C. for 2 hours with the same helium flow. A quantity of 10.11 grams of zeolite containing 3.57 wt % tungsten carbide was recovered.

Catalyst G- Zeolite with Molybdenum Promoter

A quantity of 8.3 grams of a solution of 7.7 wt % hydrated ammoniummolybdenate (($NH_4)_6Mo_7O_{24} \cdot 4H_2O$) was mixed with 15.0 grams of Catalyst D and treated at a temperature of 538° C. for 6 hours. A quantity of 15.2 grams of zeolite containing 2.28 wt % molybdenum was recovered.

EXAMPLE IV

For each of the runs below a catalyst sample of 1/16 inch extrudate was placed into a stainless steel tube reactor (length: about 18 inches; inner diameter about 0.5 inch). A hydrogen flow of 0.30 CFH at 500 psig was established and the temperature raised to approximately 900° F. (482° C.). Toluene containing a sulfur content of 200.3 ppm by weight (Houston Atlas Analysis) was introduced at a rate of 40 mL/hr (4.27 WHSV) and conditions held steady for the total on stream time. The effluent was sampled periodically and analyzed by gas chromatography. The analyses reported in Table II below are of the samples taken at the end of the run.

Catalyst D- Zeolite with No Promoter

A 7.2 gm sample of zeolite catalyst was employed for a total on stream time of 161 hours.

Catalyst E- Zeolite with Platinum Promoter

A 8.1 gm sample of zeolite catalyst was employed for a total on stream time of 144 hours.

Catalyst F- Zeolite with Tungsten Carbide Promoter

A 9.7 gm sample of zeolite catalyst was employed for a total on stream time of 144 hours.

Catalyst G- Zeolite with Molybdenum Promoter

A 9.1 gm sample of zeolite catalyst was employed for a total on stream time of 173 hours.

Table II

Disproportionation of Toluene Having Sulfur Content[1]

| Catalyst | Promoter | Toluene % Converted | Benzene Wt %[2] | Xylenes Wt %[2] |
|---|---|---|---|---|
| D (Control) | None | 28.64 | 11.61 | 15.02 |
| E (Control) | Pt | 27.80 | 10.79 | 16.28 |
| F (Invention) | $W_2C$ | 49.94 | 22.35 | 25.48 |
| G (Control) | Mo | 26.41 | 11.34 | 14.72 |

[1]Sulfur Content (Houston Atlas Analysis) 200.3 ppm by weight
[2]Wt % of Product Toluene disproportionation was compared for catalyst based on the same HZSM-5 zeolite with and without promoter metal content. The control catalysts which had no promoter in Catalyst D; platinum, a noble metal known to be deactivated by the presence of sulfur, as the promoter in Catalyst E and molybdenum- a metal of Group VIB, a Group commonly recognized as sulfur tolerant/resistant- in Catalyst G all yielded similar results in terms of the toluene converted and the weight percent of benzene and xylenes in the product. Use of the tungsten carbide promoter of this invention, Catalyst F, converted almost twice as much toluene and produced about twice as much benzene and about 60 percent more xylenes as compared to the controls.

Reasonable variations, modifications and adaptations can be made within the scope of the disclosure and the appended claims without departing from the scope of this invention.

That which is claimed is:

1. A method for the disproportionation of toluene comprising contacting toluene feedstock with a catalyst composition comprising a zeolite impregnated with tungsten carbide under conditions suitable for disproportionation of toluene comprising contacting the toluene feedstock and the catalyst composition in a conversion reaction zone at a reaction temperature in the range of from about 350° C. to about 600° C., a pressure in the range from subatmospheric up to about 1000 psia and a WHSV of the feed to the contacting zone in the range of from about 0.25 hour$^{-1}$ to about 250 hour$^{-1}$.

2. A method for the disproportionation of toluene according to claim 1 wherein the zeolite is a silica-bound zeolite prepared by calcining a mixture of zeolite and silica.

3. A method for the disproportionation of toluene according to claim 2 wherein the zeolite is a silica-bound ZSM-5 zeolite prepared by calcining a mixture of ZSM-5 zeolite and silica.

4. A method for the disproportionation of toluene according to claim 3 wherein the silica-bound ZSM-5 zeolite has been subjected to an elevated temperature in the range of about 250° C. to about 800° C. for a time period of about 0.1 hour to about 30 hours and a pressure in the range of from below atmospheric pressure to about 1000 pounds per square inch absolute (psia) in the presence of a gas selected from the group consisting of inert gases, reducing gases, air, oxygen and steam prior to impregnation with tungsten carbide.

5. A method for the disproportionation of toluene according to claim 4 wherein the impregnation of the heat treated zeolite with tunasten carbide has been accomplished using an impregnating composition selected from the group consisting of aqueous and non-agueous solutions containing tungsten.

6. A method for the disproportionation of toluene according to claim 5 wherein the impregnating composition comprises tungsten in a form of a non-aqueous solution formed by dissolving a tungsten salt in an ethanolic solution of guanadine hydrochloride.

7. A method for the disproportionation of toluene according to claim 6 wherein the tungsten salt is tungsten hexachloride.

8. A method for the disproportionation of toluene according to claim 7 wherein the weight percent of tungsten present in the impregnated zeolite is in a range of up to about 10 weight percent of the impregnated zeolite.

9. A method for the disproportionation of toluene according to claim 8 wherein the weight percent of tungsten present in the impregnated zeolite is in a range of about 0.05 to about 8 weight percent of the impregnated zeolite.

10. A method for the disproportionation of toluene according to claim 9 wherein the weight percent of tungsten present in the impregnated zeolite is in a range of about 0.1 to about 6 weight percent of the impregnated zeolite.

11. A method for the disproportionation of toluene according to claim 8 wherein the catalyst composition has been subjected to an elevated temperature in the range of about 500° C. to about 1000° C. and a pressure in the range of from below atmospheric pressure to about 1000 pounds per square inch absolute (psia) in the presence of a gas selected from the group consisting of inert gases, reducing gases, air, oxygen, nitrogen, steam and mixtures thereof for a time period of about 0.1 hour to about 30 hours.

12. A method for the disproportionation of toluene according to claim 9 wherein the catalyst composition has been subjected to an elevated temperature in the range of about 500° C. to about 1000° C. and a pressure in the range of from below atmospheric pressure to about 1000 pounds per square inch absolute (psia) in the presence of a gas selected from the group consisting of inert gases, reducing gases, air, oxygen, nitrogen, steam and mixtures thereof for a time period of about 0.1 hour to about 30 hours.

13. A method for the disproportionation of toluene according to claim 10 wherein the catalyst composition has been subjected to an elevated temperature in the range of about 500° C. to about 1000° C. and a pressure in the range of from below atmospheric pressure to about 1000 pounds per square inch absolute (psia) in the presence of a gas selected from the group consisting of inert gases, reducing cases, air, oxygen, nitrogen, steam and mixtures thereof for a time period of about 0.1 hour to about 30 hours.

* * * * *